United States Patent
Souleymanou et al.

(10) Patent No.: US 10,526,302 B2
(45) Date of Patent: Jan. 7, 2020

(54) METHOD FOR PRODUCING 5-HYDROXYMETHYLFURFURAL IN THE PRESENCE OF A LEWIS ACID CATALYST AND/OR A HETEROGENEOUS BASE CATALYST AND A HOMOGENEOUS ORGANIC BRøNSTED ACID CATALYST IN THE PRESENCE OF AT LEAST ONE APROTIC POLAR SOLVENT

(71) Applicant: IFP Energies Nouvelles, Rueil-Malmaison (FR)

(72) Inventors: Myriam Souleymanou, Neuilly Plaisance (FR); Marc Jacquin, Lyons (FR); Damien Delcroix, St Maurice L Exil (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 15/772,592

(22) PCT Filed: Oct. 17, 2016

(86) PCT No.: PCT/EP2016/074901
§ 371 (c)(1),
(2) Date: May 1, 2018

(87) PCT Pub. No.: WO2017/076625
PCT Pub. Date: May 11, 2017

(65) Prior Publication Data
US 2019/0092740 A1  Mar. 28, 2019

(30) Foreign Application Priority Data
Nov. 2, 2015 (FR) ..................... 15 60459

(51) Int. Cl.
*C07D 307/48* (2006.01)
*C07D 307/50* (2006.01)

(52) U.S. Cl.
CPC ......... *C07D 307/50* (2013.01); *C07D 307/48* (2013.01)

(58) Field of Classification Search
CPC ..................................... C07D 307/50
USPC ......................................... 549/488
See application file for complete search history.

(56) References Cited

U.S. PATENT DOCUMENTS

| 2010/0004437 A1 | 1/2010 | Binder et al. |
| 2013/0158254 A1 | 6/2013 | Binder et al. |
| 2013/0178617 A1 | 7/2013 | Raines et al. |
| 2014/0235851 A1 | 8/2014 | Binder et al. |

FOREIGN PATENT DOCUMENTS

WO    WO2013/043131 A1 *  3/2013

OTHER PUBLICATIONS

International Search Report dated Nov. 30, 2016 issued in corresponding PCT/EP2016/074901 application (3 pages).
J. Fu et al., "Catalytic Decomposition of Glucose to Levulinic Acid by Synergy of Organic Lewis Acid and Bronsted Acid in Water", BioResources, vol. 10, No. 1 (2015) pp. 1346-1356.
J. Tuteja et al., "One-Pot Synthesis of Furans From Various Saccharides Using a Combination of Solid Acid and Base Catalysts", Bulletin of the Chemical Society of Japan, vol. 85, No. 3 (2012) pp. 275-281.
G. Tian et al., "Tin-Catalyzed Efficient Conversion of Carbohydrates for the Production of 5-Hydroxymethylfurfural in the Presence of Quaternary Ammonium Salts", Carbohydrate Research, vol. 370 (2013) pp. 33-37.

* cited by examiner

*Primary Examiner* — Taylor V Oh
(74) *Attorney, Agent, or Firm* — Millen White Zelano and Branigan, PC; Csaba Henter

(57) ABSTRACT

The invention relates to a process for the production of 5-hydroxymethylfurfural from a feedstock comprising at least one sugar using a combination of at least one catalyst selected from the homogeneous Lewis acids, the heterogeneous Lewis acids and the heterogeneous bases and at least one homogeneous Brønsted acid catalyst selected from the families of the thioureas, the sulphonic acids and the phosphorus-containing organic compounds, alone or in a mixture, in the presence of at least one aprotic polar solvent, at a temperature comprised between 30° C. and 300° C., and at a pressure comprised between 0.1 MPa and 10 MPa.

20 Claims, No Drawings

METHOD FOR PRODUCING 5-HYDROXYMETHYLFURFURAL IN THE PRESENCE OF A LEWIS ACID CATALYST AND/OR A HETEROGENEOUS BASE CATALYST AND A HOMOGENEOUS ORGANIC BRøNSTED ACID CATALYST IN THE PRESENCE OF AT LEAST ONE APROTIC POLAR SOLVENT

TECHNICAL FIELD OF THE INVENTION

The invention relates to a process for the conversion of sugars and in particular hexoses to 5-hydroxymethylfurfural in the presence of a combination of at least one catalyst selected from the homogeneous Lewis acids, the heterogeneous Lewis acids and the heterogeneous bases and at least one homogeneous Brønsted acid catalyst selected from the families of the thioureas, the sulphonic acids and the phosphorus-containing organic compounds, alone or in a mixture, in the presence of at least one aprotic polar solvent.

PRIOR ART 5-hydroxymethylfurfural (5-HMF) is a compound derived from biomass which can be reused in many fields as a precursor of active ingredients in pharmacy, agricultural chemistry or speciality chemicals. During the last few years, it has been used to advantage as a precursor of furandicarboxylic acid (FDCA), which is used as a substitute for terephthalic acid as a monomer for the production of polyester fibres or consumer plastics.

The production of 5-HMF by dehydration of hexoses has been known for many years and has been the subject of a significant number of research studies. On the one hand, the dehydration of galactose to 5-HMF is described in an aprotic polar solvent, for example dimethylacetamide doped with lithium chloride and an ionic liquid in patent application US 2010/0004437, in the presence of a combination of chromium chloride and sulphuric acid with performances corresponding to yields of 5-HMF less than 10%. On the other hand, the dehydration of another sugar such as glucose to 5-HMF is described in a protic polar solvent, for example water, in Fu et al., Bioresources, 2015, 10, 1346, in the presence of a combination of an aluminium triflate and oxalic acid with the majority formation of unwanted products during the synthesis of 5-HMF such as levulinic acid and a yield of 5-HMF less than 10%. The dehydration of glucose is also described in water by Vlachos et al., Green Chem, 2015, 17, 4693, in the presence of a combination of chromium chloride and hydrochloric acid with the majority formation of unwanted products during the synthesis of 5-HMF such as levulinic acid and a maximum yield of 5-HMF of 50%.

Thus, there is a need for the development of new processes for the selective conversion of sugars to 5-HMF making it possible to obtain improved yields without the formation of unwanted by-products.

Surprisingly, the applicant has demonstrated that contacting sugars with a combination of at least one catalyst selected from the homogeneous Lewis acids, the heterogeneous Lewis acids and the heterogeneous bases and at least one homogeneous Brønsted acid catalyst selected from the families of the thioureas, the sulphonic acids and the phosphorus-containing organic compounds, alone or in a mixture, in the presence of at least one aprotic polar solvent made it possible to significantly increase the 5-HMF yields, while limiting the formation of unwanted by-products.

Thus, the invention relates to a process for the production of 5-hydroxymethylfurfural from a feedstock comprising at least one sugar using a combination of at least one catalyst selected from the homogeneous Lewis acids, the heterogeneous Lewis acids and the heterogeneous bases and at least one homogeneous Brønsted acid catalyst selected from the families of the thioureas, the sulphonic acids and the phosphorus-containing organic compounds, alone or in a mixture, in the presence of at least one aprotic polar solvent.

SUBJECT OF THE INVENTION

A subject of the present invention is therefore to provide a novel process for the conversion of a feedstock comprising at least one sugar to 5-hydroxymethylfurfural, in which said feedstock is contacted with a combination of at least one catalyst selected from the homogeneous Lewis acids, the heterogeneous Lewis acids and the heterogeneous bases and at least one homogeneous Brønsted acid catalyst selected from the families of the phosphorus-containing organic compounds, the thioureas, the sulphonic acids, alone or in a mixture in the presence of at least one aprotic polar solvent, at a temperature comprised between 30° C. and 300° C., and at a pressure comprised between 0.1 MPa and 10 MPa.

By Brønsted acid is meant a molecule from the family of Brønsted acids bearing at least one acid function.

By homogeneous catalyst is meant a catalyst that is soluble in the reaction medium.

By heterogeneous catalyst is meant a catalyst that is insoluble in the reaction medium.

By aprotic solvent is meant a molecule acting as a solvent, all the hydrogens of which are borne by carbons.

By polar solvent is meant a molecule acting as a solvent, the dipole moment $\mu$ of which expressed in Debye has a numerical value greater than or equal to 2.00 measured at 25° C.

Thus, by aprotic polar solvent is meant a molecule acting as a solvent, all the hydrogens of which are borne by carbons, and the dipole moment $\mu$ of which expressed in Debye has a numerical value greater than or equal to 2.00 measured at 25° C.

An advantage of the present invention is to provide a process for the conversion of sugars to 5-hydroxymethylfurfural using a combination of at least one catalyst selected from the homogeneous Lewis acids, the heterogeneous Lewis acids and the heterogeneous bases and at least one homogeneous Brønsted acid catalyst selected from the families of the thioureas, the sulphonic acids and the phosphorus-containing organic compounds, alone or in a mixture, in the presence of at least one aprotic polar solvent and limiting the production of unwanted by-products such as humins. The humins are condensation by-products resulting from the degradation of the sugars in an acid medium such as polyfurans.

DETAILED DESCRIPTION OF THE INVENTION

The Feedstock

The feedstock treated in the process according to the invention is a feedstock comprising at least one sugar, preferably selected from the polysaccharides, the oligosaccharides and the monosaccharides, alone or in a mixture.

By monosaccharide is meant more particularly the carbohydrates of general formula $C_6(H_2O)_6$ or $C_6H_{12}O_6$. The preferred monosaccharides used as feedstock in the present invention are selected from glucose, mannose, fructose, used alone or in a mixture.

By oligosaccharide is meant more particularly a carbohydrate having the empirical formula $C_{6n}H_{10n+2}O_{5n+1}$ where n is an integer greater than 1, the monosaccharide units composing said oligosaccharide being identical or not, and/ or a carbohydrate having the empirical formula $(C_{6m}H_{10m+2}O_{5m+1})(C_{5n}H_{8n+2}O_{4n+1})$ where m and n are integers greater than or equal to 1, the monosaccharide units composing said oligosaccharide being identical or not.

The oligosaccharides are preferably selected from the oligomers of hexoses or pentoses and hexoses, preferably from the oligomers of hexoses, preferably with a degree of polymerization allowing them to be soluble under the reaction conditions envisaged by the invention. They can be obtained by partial hydrolysis of polysaccharides originating from renewable resources such as starch, inulin, cellulose or hemicellulose, optionally originating from lignocellosic biomass. For example, steam explosion of lignocellosic biomass is a process of partial hydrolysis of the cellulose and hemicellulose contained in the lignocellosic biomass producing a flow of oligo- and monosaccharides.

The preferred oligosaccharides used as feedstock in the present invention are preferably selected from saccharose, lactose, maltose, isomaltose, inulobiose, melibiose, gentiobiose, trehalose, cellobiose, cellotriose, cellotetraose and the oligosaccharides originating from hydrolysis of said polysaccharides originating from the hydrolysis of starch, inulin, cellulose or hemicellulose, used alone or in a mixture.

By polysaccharide is meant more particularly the polysaccharide(s) selected from starch, inulin, lignocellosic biomass, cellulose and hemicellulose, alone or in a mixture.

Starch $(C_6H_{10}O_5)_n$ is found in large quantities in the storage organs of many plants: the cereals, legumes, roots, tubers and rhizomes, and fruits.

Inulin $C_{6n}H_{10n+2}O_{5n+1}$, like starch, is an energy storage means for plants and is found more particularly in the roots of the asteraceae.

Lignocellosic biomass is essentially constituted by three natural components present in variable quantities according to its origin: cellulose, hemicellulose and lignin. It is found in all plants: herbage, branches, agricultural residues, trees, maize plants, etc.

Cellulose $(C_6H_{10}O_5)_n$ represents the major part (40-60%) of the composition of the lignocellosic biomass. Cellulose is insoluble in water at ambient temperature and pressure.

Hemicellulose constitutes 20 to 40% by weight of lignocellosic biomass. Unlike cellulose, this polymer is constituted by a majority of monomers of pentoses (rings with 5 atoms) and hexoses (rings with 6 atoms). Hemicellulose is an amorphous heteropolymer with a lesser degree of polymerization than that of cellulose (30-100), and is generally soluble in water.

Lignocellosic biomass can be used as feedstock in the present invention following any pre-treatment known to a person skilled in the art.

Preferably, the feedstock comprising at least one sugar used in the process according to the invention is selected from cellulose, hemicellulose, starch, inulin, cellobiose, saccharose, fructose and glucose, used alone or in a mixture.

Very preferably, said feedstock is selected from cellulose, starch, glucose and fructose, used alone or in a mixture.

The Catalysts

According to the invention, said feedstock is contacted, in the process according to the invention, with a combination of at least one catalyst selected from the homogeneous Lewis acids, the heterogeneous Lewis acids and the heterogeneous bases and at least one homogeneous Brønsted acid catalyst selected from the families of the thioureas, the sulphonic acids and the phosphorus-containing organic compounds, alone or in a mixture, in the presence of at least one aprotic polar solvent, at a temperature comprised between 30° C. and 300° C., and at a pressure comprised between 0.1 MPa and 10 MPa.

According to the invention, at least one of the catalysts is selected from the homogeneous Lewis acids, the heterogeneous Lewis acids and the heterogeneous bases.

The homogeneous Lewis acids are selected from the compounds of formula $M_mX_n$, solvated or not, in which M is an atom selected from the atoms of groups 3 to 16 of the periodic table, including lanthanides, m is an integer comprised between 1 and 10, n is an integer comprised between 1 and 10 and X is an anion selected from the hydroxides, halides, nitrates, carboxylates, halocarboxylates, acetylacetonates, alcoholates, phenolates, substituted or not, the sulphates, alkylsulphates, phosphates, alkylphosphates, halosulphonates, alkylsulphonates, per-haloalkylsulphonates, bis(per-haloalkylsulphonyl)amides, arenesulphonates, substituted or not by halogen or haloalkyl groups, said anions X being able to be identical or different in the case where n is greater than 1.

Preferably, the homogeneous Lewis acids are selected from the compounds of formula $M_mX_n$, solvated or not, in which M is an atom selected from the atoms of groups 6 to 13 of the periodic table, including lanthanides, m is an integer comprised between 1 and 5, n is an integer comprised between 1 and 5 and X is an anion selected from the halides, sulphates, alkylsulphonates, per-haloalkylsulphonates, substituted or not by halogen or haloalkyl groups, said anions X being able to be identical or different in the case where n is greater than 1.

Preferably, the homogeneous Lewis acids are selected from $BF_3$, $AlCl_3$, $Al(OTf)_3$, $FeCl_3$, $ZnCl_2$, $SnCl_2$, $CrCl_3$, $CeCl_3$ and $ErCl_3$.

The heterogeneous Lewis acids are selected from the simple or mixed oxides of the compounds selected from silicon, aluminium, zirconium, titanium, niobium, tungsten, doped or not with an element selected from tin, tungsten and hafnium and from the phosphates of the metals, said metals being selected from niobium, zirconium, tantalum, tin and titanium.

Preferably, the heterogeneous Lewis acids are selected from zirconium oxides, titanium oxides, mixed oxides of aluminium and silicon doped with tin such as the zeolite Sn-β or the mesostructured silica Sn-MCM-41, tin and titanium phosphates.

The heterogeneous bases are selected from the basic solids known to a person skilled in the art, and preferably selected from the perovskites of formula $ABO_3$ in which A is selected from the elements Mg, Ca, Sr and Ba, and B is selected from the elements Fe, Mn, Ti and Zr, the oxides of the elements selected from lanthane (La), neodymium (Nd), yttrium (Y), cerium (Ce), alone or in a mixture, said oxides being able to be doped with at least one element selected from the alkali metals, the alkaline-earth and the rare-earth metals, alone or in a mixture, the zeolites exchanged with alkali metals, alkaline earth and rare earth metals, alkaline hydrotalcites, alkali metal silicates containing, or not containing, alkali metals, alkaline earth and rare earth metals.

Preferably, the heterogeneous bases are selected from perovskite $BaZrO_3$, rare earth oxide $CeO_2$, zeolite Na—X, hydrotalcite "Mg—Al" $Mg_6Al_2(OH)_{16}(CO_3)_4H_2O$, titanosilicate ETS-10 and sodium-yttrium-silicate AV-1.

According to the invention, the homogeneous Brønsted acid catalysts are selected from the families of the phosphorus-containing organic compounds, the thioureas and the sulphonic acids, alone or in a mixture.

In the case where the homogeneous Brønsted acid catalyst is selected from the family of the phosphorus-containing organic compounds it corresponds to the general formula:

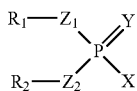

in which:
- X is an OH, SH, SeH or $NHR_3$ group with $R_3$ selected from the aryl, aryl sulphonyl and trifluoromethanesulphonyl groups,
- Y is an oxygen, sulphur or selenium atom,
- $Z_1$ and $Z_2$, identical or different, are either an oxygen atom, or an $NR_4$ group with $R_4$ selected from trifluoromethanesulphonyl, p-toluenesulphonyl and 2-naphthalenesulphonyl,
- $R_1$ and $R_2$, identical or different, are selected from the alkyl groups, being able to be substituted or not, linear or branched, cyclic or non-cyclic, and the aryl groups, being able to be substituted or not, fused or not.

Preferably, X is an OH, SH or $NHR_3$ group, $R_3$ having the above definition. More preferably, X is an OH or $NHR_3$ group, $R_3$ having the above definition. More preferably, X is an $NHR_3$ group, $R_3$ having the above definition.

In the case where X is an $NHR_3$ group with $R_3$ selected from the haloalkylsulphonyls, $R_3$ is preferably trifluoromethanesulphonyl.

Preferably, Y is a sulphur or an oxygen. More preferably, Y is an oxygen.

In the case where $Z_1$ and/or $Z_2$ is(are) an $NR_4$ group, $R_4$ is advantageously selected from the arylsulphonyls and the haloalkylsulphonyls, and very preferably from trifluoromethanesulphonyl, p-toluenesulphonyl and 2-naphthenesulphonyl.

Preferably, $Z_1$ and $Z_2$ are identical.

The $R_1$ and $R_2$ groups can be independently selected from the aryl and alkyl groups. For example, $R_1$ can be selected from the aryl groups and $R_2$ from the alkyl groups.

In the case where said $R_1$ and $R_2$ groups are selected from the aryl groups, they are advantageously selected from the aryl groups having 6 to 14 carbon atoms, fused or not.

Preferably, the aryl groups having 6 to 14 carbon atoms are selected from the phenyl, naphthyl, phenanthryl and anthryl groups, and very preferably, said aryl group is phenyl.

Preferably, $R_1$ and $R_2$ are selected from the aryl groups and are identical.

In the case where said $R_1$ and $R_2$ groups are selected from the alkyl groups, they are advantageously selected from the alkyl groups having 1 to 12 carbon atoms, and preferably having 1 to 6 carbon atoms, and the cycloalkyl groups having 3 to 6 carbon atoms, and preferably having 5 to 6 carbon atoms.

Preferably, the non-cyclic alkyl groups having 1 to 12 carbon atoms, and preferably 1 to 6 carbon atoms, linear or branched, are selected from the methyl, ethyl, propyl, butyl, pentyl and hexyl groups.

Preferably, the cycloalkyl groups having 3 to 6 carbon atoms, and preferably 5 to 6 carbon atoms are selected from the cyclopentyl and cyclohexyl groups.

In the case where said $R_1$ and $R_2$ groups are substituted, they are preferably substituted with at least one group selected from the halogens, the $-CX_3$ groups with X being a halogen and preferably fluorine, the nitro group $-NO_2$, the $-NHCOCH_3$ group, the alkoxy groups, preferably selected from the methoxy and ethoxy groups, the alkyl groups having 1 to 12 carbon atoms, linear or branched, cyclic or non-cyclic, preferably selected from the methyl, ethyl, propyl, butyl, pentyl and hexyl groups and the aryl groups, optionally substituted, selected from the phenyls, biphenyls, naphthyls, anthryls and phenanthryls.

Preferably, said $R_1$ and $R_2$ groups are substituted with at least one group selected from the trifluoromethyl, cyclohexyl, cyclopentyl and phenyl groups.

In an embodiment, $R_1$ and $R_2$ are bonded together. When $R_1$ and $R_2$ are bonded together, this can be covalently or by a carbon atom in common.

By bonded covalently is meant the case where a covalent bond connects the $R_1$ and $R_2$ groups. For example $R_1$ and $R_2$ can be phenyls bonded together in order to form a biphenyl (Formula 1) or $R_1$ and $R_2$ together form a divalent group, such as an alkylene, a cycloalkylene or also an arylene (Formula 2).

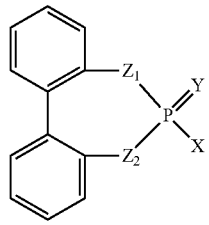

Formula 1

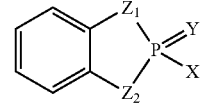

Formula 2

By bonded by a carbon atom in common is meant when $R_1$ and $R_2$ have structures that are identical or different which share a carbon atom. For example $R_1$ and $R_2$ can be phenyls bonded together by a spiro[4,4]nonane group (Formula 3).

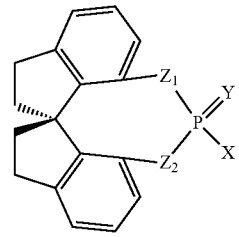

Formula 3

Advantageously in the case where the homogeneous Brønsted acid catalyst is selected from the family of the phosphorus-containing organic compounds it is selected from the following catalysts: the diphenylphosphate corresponding to the formula called phosphorus-containing compound 1 and the N-triflyl-diphenylphosphoramide corresponding to the formula called phosphorus-containing compound 2. The names phosphorus-containing compound 1 and phosphorus-containing compound 2 are specific to the text and are intended to make it simpler to refer to these organic catalysts, the formulae of which are given below:

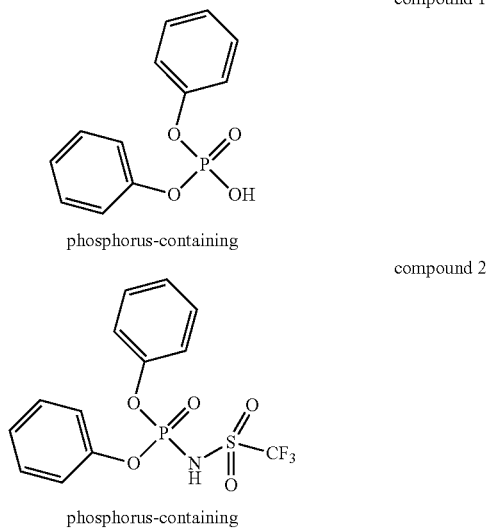

compound 1 phosphorus-containing compound 2 phosphorus-containing

In the case where the homogeneous Brønsted acid catalyst is selected from the family of the thioureas it corresponds to the general formula:

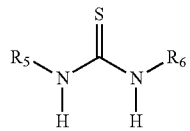

in which the $R_5$ and $R_6$ groups are selected from the aromatic groups comprising a heteroatom or not, the linear or branched groups, cyclic or non-cyclic, and the alkyl groups containing at least one heteroatom, linear or branched, cyclic or non-cyclic, said $R_5$ and $R_6$ groups being able to be substituted or not and identical or different.

The $R_5$ and $R_6$ groups can be independently selected from the families of groups. For example, $R_5$ can be selected from the aromatic groups and $R_6$ from the cycloalkyl groups.

In the case where $R_5$ and $R_6$ are selected from one and the same group family, $R_5$ and $R_6$ can be identical or different.

Preferably, said $R_5$ and $R_6$ groups are selected from the aromatic groups comprising a heteroatom or not, and the alkyl groups, cyclic or non-cyclic, said $R_5$ and $R_6$ groups being able to be substituted or not and identical or different, and preferably, said $R_5$ and $R_6$ groups are selected from the aromatic groups not comprising heteroatoms.

In the case where said $R_5$ and $R_6$ groups are selected from the aromatic groups comprising a heteroatom, said heteroatom is preferably selected from nitrogen, phosphorus and oxygen. In this case said $R_5$ and $R_6$ groups are preferably selected from the pyridine, phosphole and furan groups.

In the case where said $R_5$ and $R_6$ groups are selected from the aromatic groups not comprising a heteroatom, they are advantageously selected from the aromatic groups having 6 to 14 carbon atoms, fused or not.

Preferably, the aromatic groups having 6 to 14 carbon atoms are selected from the phenyl, naphthyl, phenanthryl and anthryl groups, and very preferably, said group is phenyl.

In the case where said $R_5$ and $R_6$ groups are selected from the alkyl groups, linear or branched, cyclic or non-cyclic, they are advantageously selected from the alkyl groups having 1 to 12 carbon atoms, and preferably having 1 to 6 carbon atoms, and the cycloalkyl groups having 3 to 8 carbon atoms, and preferably having 5 to 8 carbon atoms.

Preferably, the non-cyclic alkyl groups having 1 to 12 carbon atoms, and preferably 1 to 6 carbon atoms, linear or branched, are selected from the methyl, ethyl, propyl, iso-propyl, butyl, pentyl and hexyl groups.

Preferably, the cycloalkyl groups having 3 to 8 carbon atoms, and preferably having 5 to 8 carbon atoms are selected from the cyclopentyl, cyclohexyl, cycloheptyl and bicyclo[2.2.2]octyl groups.

In the case where said $R_5$ and $R_6$ groups are selected from the alkyl groups comprising at least one heteroatom, cyclic or non-cyclic, said heteroatom is preferably selected from nitrogen.

Said groups are thus advantageously selected from the alkyl and/or cycloalkyl groups which can comprise at least one tertiary amine function. In this case, they are advantageously selected from N,N-dimethylethylamine, N,N-dimethylcyclohexylamine, N-methylpiperidine and aza-bicyclo[2.2.2]octyl.

In the case where said $R_5$ and $R_6$ groups are substituted, they are preferably substituted with at least one group selected from the halogens, the —$CX_3$ groups with X being a halogen and preferably fluorine, the nitro group —$NO_2$, the —$NHCOCH_3$ group, the alkoxy groups, preferably selected from the methoxy and ethoxy groups, the alkyl groups having 1 to 12 carbon atoms, linear or branched, preferably selected from the methyl, ethyl, propyl, butyl, pentyl and hexyl groups.

Preferably, said $R_5$ and $R_6$ groups are substituted with at least one group selected from the halogens, the —$CX_3$ groups with X being a halogen and preferably fluorine and the alkoxy groups, preferably the methoxy groups. Said $R_5$ and $R_6$ groups can advantageously be mono- or disubstituted.

Advantageously, in the case where the homogeneous Brønsted acid catalyst is selected from the family of the thioureas it is selected from the following catalysts: 1-(3,5-bis-trifluoromethyl-phenyl)-3-cyclohexylthiourea corresponding to the general formula called thiourea 1, and 1-(4-methoxyphenyl)-3-phenylthiourea corresponding to the general formula called thiourea 2. The names thiourea 1 and thiourea 2 are specific to the text and are intended to make it simpler to refer to these organic catalysts, the formulas of which are given below:

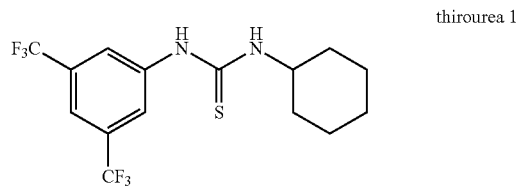

thirourea 1

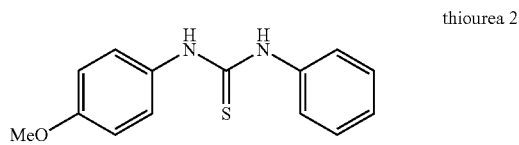

thiourea 2

In the case where the homogeneous Brønsted acid catalyst is selected from the family of the sulphonic acids it corresponds to the general formula:

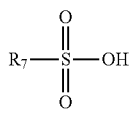

in which $R_7$ is selected from
the halogen groups,
the alkyl groups, linear or branched, cyclic or non-cyclic, comprising 1 to 20 carbon atoms being able to be substituted or not with at least one substituent selected from:
the oxo group,
the halogen groups and,
the aryl groups, fused or not, being able to be substituted or not with halogen groups and/or linear or branched, cyclic or non-cyclic alkyl groups containing 1 to 20 carbon atoms.
the aryl groups comprising 6 to 14 carbon atoms, being able to be substituted or not with at least one substituent selected from:
the alkyl groups, linear or branched, cyclic or non-cyclic, comprising 1 to 20 carbon atoms, being able to be substituted or not with at least one halogenated group or at least one nitro group,
the halogenated groups and,
the nitro group.

In the case where $R_7$ is a halogen group, said halogen group is preferably selected from fluorine, chlorine, bromine and iodine.

Preferably, in the case where $R_7$ is a halogen group, said halogen group is fluorine.

In the case where $R_7$ is a linear alkyl group, said linear alkyl group contains 1 to 20 carbon atoms, preferably 1 to 10 carbon atoms and preferably 1 to 6 carbon atoms.

Even more preferably, in the case where $R_7$ is a linear alkyl group, said linear alkyl group is selected from the methyl, ethyl and propyl groups.

Very advantageously, in the case where $R_7$ is a linear alkyl group, said linear alkyl group is methyl, and the catalyst from the family of the sulphonic acids is methanesulphonic acid.

In the case where $R_7$ is a branched alkyl group, said branched alkyl group contains 3 to 20 carbon atoms, preferably 3 to 10 carbon atoms and more preferably 3 to 6 carbon atoms.

Even more preferably, in the case where $R_7$ is a branched alkyl group, said branched alkyl group is selected from the isopropyl, isobutyl and tertbutyl groups.

In the case where $R_7$ is a cyclic alkyl group, said cyclic alkyl group contains 3 to 20 carbon atoms, preferably 5 to 8 carbon atoms.

Preferably, in the case where $R_7$ is a cyclic alkyl group, said cyclic alkyl group is selected from the cyclopentyl and cyclohexyl groups.

In the case where $R_7$ is an alkyl group substituted with at least one oxo (=O) group, said oxo group can be positioned on a terminal carbon or not. Said oxo group thus being able to form part of a ketone, aldehyde or carboxylic acid function.

Preferably, in the case where $R_7$ is an alkyl group substituted with at least one oxo (=O) group said oxo group forms part of a ketone function or an aldehyde function.

In the case where $R_7$ is an alkyl group substituted with at least one halogen group, said halogen group is preferably selected from fluorine, chlorine, bromine and iodine and preferably fluorine.

Very preferably, in the case where $R_7$ is an alkyl group substituted with at least one halogen group, $R_7$ is trifluoromethyl and the catalyst from the family of the sulphonic acids is trifluoromethanesulphonic acid.

In the case where $R_7$ is an alkyl group substituted with at least one aryl group, said aryl group is advantageously selected from phenyl, tolyl and naphthyl.

Preferably, in the case where $R_7$ is an alkyl group substituted with at least one aryl group, said aryl group is phenyl and $R_7$ is the benzyl group.

In the case where $R_7$ is an alkyl group substituted with at least one aryl group, said alkyl group is advantageously substituted with at least one halogen group selected from fluorine, chlorine, bromine and iodine, preferably fluorine.

In the case where $R_7$ is an aryl group, said aryl group contains 6 to 14 carbon atoms, preferably 6 to 10 carbon atoms.

Preferably, in the case where $R_7$ is an aryl group, said aryl group is phenyl or naphthyl.

In the case where $R_7$ is an aryl group substituted with at least one halogen group, said halogen group is preferably selected from fluorine, chlorine, bromine and iodine and preferably fluorine.

In the case where $R_7$ is an aryl group substituted with at least one alkyl group, said alkyl group is advantageously selected from the linear or branched alkyls containing 1 to 6 carbon atoms.

Preferably, in the case where $R_7$ is an aryl group substituted with at least one alkyl group, said alkyl group is selected from methyl, ethyl, propyl and isopropyl.

Even more preferably, in the case where $R_7$ is an aryl group substituted with at least one alkyl group, said alkyl group is methyl and the catalyst from the family of the sulphonic acids is paratoluenesulphonic acid.

In the case where $R_7$ is an aryl group substituted with an alkyl group, said alkyl group is advantageously substituted with at least one halogen group selected from fluorine, chlorine, bromine and iodine, preferably fluorine.

In a preferred embodiment, the process according to the invention is implemented with a combination of a homogeneous Lewis acid catalyst and a homogeneous Brønsted acid catalyst in the presence of DMSO.

In the case where the process according to the invention is implemented with a combination of a homogeneous Lewis acid catalyst and a homogeneous Brønsted acid catalyst said homogeneous Lewis acid catalyst is preferably aluminium triflate and said homogeneous Brønsted acid catalyst is selected from methanesulphonic acid, the phosphorus-containing compound 2 and the thiourea compound 1.

Conversion Process

According to the invention, the process for the conversion of a feedstock comprising at least one sugar is implemented in a reaction chamber in the presence of at least one solvent, said solvent being an aprotic polar solvent or a mixture of aprotic polar solvents, at a temperature comprised between 30° C. and 300° C., and at a pressure comprised between 0.1 MPa and 10 MPa.

The process is thus implemented in a reaction chamber comprising at least one aprotic polar solvent and in which said feedstock is brought into the presence of a combination of at least one catalyst selected from the homogeneous Lewis acids, the heterogeneous Lewis acids and the heterogeneous bases and at least one homogeneous Brønsted acid catalyst according to the invention.

According to the invention, the process takes place in the presence of at least one solvent, said solvent being an aprotic polar solvent or a mixture of aprotic polar solvents.

The aprotic polar solvents are advantageously selected from all the aprotic polar solvents the dipole moment of which expressed in Debye (D) is greater than or equal to 2.00. Preferably, said solvents are selected from pyridine (2.37), butan-2-one (5.22), acetone (2.86), acetic anhydride (2.82), N,N,N',N'-tetramethylurea (3.48), benzonitrile (4.05), acetonitrile (3.45), methyl ethyl ketone (2.76), propionitrile (3.57), hexamethylphosphoramide (5.55), nitrobenzene (4.02), nitromethane (3.57), N,N-dimethylformamide (3.87), N,N-dimethylacetamide (3.72), sulpholane (4.80), N-methylpyrrolidone (4.09), dimethylsulphoxide (3.90), propylene carbonate (4.94) and γ-valerolactone (4.71).

Preferably, the aprotic polar solvents are advantageously selected from acetone, N,N-dimethylformamide, N,N-dimethylacetamide, sulpholane, N-methylpyrrolidone, dimethylsulphoxide, propylene carbonate and γ-valerolactone.

Preferably, the aprotic polar solvents are advantageously selected from N,N-dimethylacetamide, N-methylpyrrolidone, dimethylsulphoxide and γ-valerolactone.

Preferably, said process according to the invention takes place at a temperature comprised between 50° C. and 200° C. and preferably between 50° C. and 175° C., and at a pressure comprised between 0.1 MPa and 8 MPa and preferably between 0.1 and 5 MPa.

Generally, the process can be carried out according to different embodiments. Thus, the process can advantageously be carried out in batches or continuously. It can take place in a closed reactor chamber or in a semi-open reactor.

The catalyst(s) selected from the homogeneous Lewis acids, the heterogeneous Lewis acids and the heterogeneous bases are introduced into the reaction chamber at the rate of a quantity corresponding to a feedstock/catalyst(s) mass ratio comprised between 1 and 1000, preferably between 1 and 500, preferably between 1 and 200, preferably between 1 and 150.

The homogeneous Brønsted acid catalysts are introduced into the reaction chamber at the rate of a quantity corresponding to a feedstock/catalyst(s) mass ratio comprised between 1 and 1000, preferably between 1 and 500, preferably between 1 and 200, preferably between 1 and 150.

The feedstock is introduced into the process at the rate of a quantity corresponding to a solvent/feedstock mass ratio comprised between 0.1 and 200, preferably between 0.3 and 100 and more preferentially between 1 and 50.

If a continuous process is selected, the mass hourly velocity (mass flow of feedstock/weight of catalyst) is between 0.01 $h^{-1}$ and 5 $h^{-1}$, preferably between 0.02 $h^{-1}$ and 2 $h^{-1}$.

Products Obtained and Method of Analysis Thereof

The product of the reaction of the conversion process according to the invention is 5-hydroxymethylfurfural.

At the end of the reaction, the reaction medium is analyzed by gas chromatography (GC) in order to determine the 5-HMF content in the presence of an internal standard and by ionic chromatography in order to determine the conversion of the feedstock in the presence of an external standard and in order to quantify the unwanted products such as levulinic acid, formic acid and humins.

EXAMPLES

In the examples below, the glucose used as feedstock is commercial and used without additional purification.

The dimethylsulphoxide, denoted DMSO in the examples, used as an aprotic polar solvent, is commercial and is used without additional purification.

The aluminium triflate and methanesulphonic acid denoted MSA in the examples are commercial and are used without additional purification.

The chlorodiphenylphosphate, trifluoromethanesulphonamide, triethylamine and 2,4-dimethylaminopyridine used for the synthesis of the phosphorus-containing compound 2 are commercial and are used without additional purification.

The 3,5-trifluoromethylphenyl isothiocyanate and cyclohexylamine used for the synthesis of the thiourea compound 1 are commercial and are used without additional purification.

For Examples 1 and 2 of preparation of the phosphorus-containing compound 2 and thiourea compound 1, the molar yield in the compound is calculated by the ratio between the number of moles of compound obtained and the number of moles of limiting reagent used.

For Examples 3 to 9 of the conversion of sugars to 5-HMF, the molar yield of 5-HMF is calculated by the ratio between the number of moles of 5-HMF obtained and the number of moles of feedstock used.

Example 1: Preparation of the Phosphorus-Containing Compound 2

Triethylamine (5.0 mL, 37.78 mmol), dimethylaminopyridine (1.294 g, 10.60 mmol) and trifluoromethanesulphonamide (0.948 g, 6.36 mmol) are added successively to a solution formed of chlorodiphenyl phosphate (1.426 g, 5.31 mmol) and dichloromethane (20 mL) maintained at 0° C. The reaction medium is returned to ambient temperature under stirring for 2 h, the solvent taken to reflux for 1 h. At the end of heating, monitoring the progress of the reaction by NMR $^{31}$P spectroscopy shows total conversion of chlorodiphenyl phosphate and the appearance of a majority product at −12.72 ppm. After return to ambient temperature, the reaction medium is diluted in water and extracted with dichloromethane. The organic phase is washed with a 37% aqueous solution of hydrochloric acid. The aqueous phase is re-extracted with dichloromethane. After washing the organic phases with a saturated aqueous solution of NaCl, the latter are combined, dried over anhydrous magnesium sulphate, filtered and evaporated under vacuum. The crude product obtained is dissolved in a minimum of dichloromethane and recrystallized cold. The weight of phosphorus-containing compound 2 obtained is 0.75 g. The corresponding molar yield of phosphorus-containing compound 2 is 37% after purification.

Empirical formula: $C_{13}H_{11}NO_5PS$ Molecular weight: 381.26 g·mol$^{-1}$

NMR $^{19}$F (δ (ppm), (CD$_2$Cl$_2$, 282 MHz) −77.26 (s) ppm
NMR $^{31}$P (δ (ppm), (CD$_2$Cl$_2$, 121 MHz) −16.4 (s) ppm
NMR $^{1}$H (δ (ppm), (CD$_2$Cl$_2$, 300 MHz) 7.40-7.16 (m, 10H), 6.67 (br.s, 1H)

Example 2: Preparation of the Thiourea Compound 1

3,5-trifluoromethylphenyl isothiocyanate (1.485 g, 5.5 mmol) and cyclohexylamine (0.595 g, 6 mmol) are dissolved in anhydrous dichloromethane and the reaction medium is stirred overnight at ambient temperature. The solvent is then evaporated off under vacuum and the crude product obtained is purified by silica column chromatography, the mobile phase being of $CH_2Cl_2$/MeOH gradient. The weight of thiourea compound 1 obtained is 0.83 g. The corresponding molar yield of thiourea compound 1 is 41% after purification.

Empirical formula: $C_{15}H_{16}F_6N_2S$ Molar weight: 370.09 g·mol$^{-1}$

NMR$^1$H (δ (ppm), $(CD_3)_2CO$, 300 MHz) 8.29 (s, 2H), 7.67 (s, 1H), 4.35-4.15 (m, 1H), 1.81-1.54 (m, 4H), 1.45-1.08 (m, 6H)

Example 3: Conversion of Glucose Utilizing Aluminium Triflate Al(OTf)$_3$ in DMSO (Not According to the Invention)

Aluminium triflate Al(OTf)$_3$ (0.26 g, 0.54 mmol) is added to a solution of glucose (2.0 g, 11.10 mmol) in DMSO (20 g). The feedstock/Lewis acid catalyst mass ratio is 8. The solvent/feedstock mass ratio is 10. The reaction medium is then stirred at 120° C. for 6 h. The conversion of glucose to 5-HMF is monitored by regular sampling of an aliquot of solution which is immediately cooled to 0° C., redissolved in water and tested by ionic chromatography. The molar yield of 5-HMF after 6 h is 64%. The yield of unwanted humins is 36%.

Example 4: Conversion of Glucose Utilizing Methanesulphonic Acid in DMSO (Not According to the Invention)

Methanesulphonic acid (0.018 g, 0.19 mmol) is added to a solution of glucose (2.0 g, 11.10 mmol) in DMSO (20 g). The feedstock/Brønsted acid catalyst mass ratio is 111. The solvent/feedstock mass ratio is 10. The reaction medium is then stirred at 120° C. for 6 h. The conversion of glucose to 5-HMF is monitored by regular sampling of an aliquot of solution which is immediately cooled to 0° C., redissolved in water and tested by ionic chromatography. The molar yield of 5-HMF after 6 h is 61%. The yield of unwanted humins is 39%.

Example 5: Conversion of Glucose Utilizing the Phosphorus-Containing Compound 2 in DMSO (Not According to the Invention)

The phosphorus-containing compound 2 (0.072 g, 0.19 mmol) is added to a solution of glucose (2.0 g, 11.10 mmol) in DMSO (20 g). The feedstock/Brønsted acid catalyst mass ratio is 28. The solvent/feedstock mass ratio is 10. The reaction medium is then stirred at 120° C. for 6 h. The conversion of glucose to 5-HMF is monitored by regular sampling of an aliquot of solution which is immediately cooled to 0° C., redissolved in water and tested by ionic chromatography. The molar yield of 5-HMF after 6 h is 60%. The yield of unwanted humins is 40%.

Example 6: Conversion of Glucose Utilizing the Thiourea Compound 1 in DMSO (Not According to the Invention)

The thiourea compound 1 (0.070 g, 0.19 mmol) is added to a solution of glucose (2.0 g, 11.10 mmol) in DMSO (20 g). The feedstock/Brønsted acid catalyst mass ratio is 29. The solvent/feedstock mass ratio is 10. The reaction medium is then stirred at 120° C. for 6 h. The conversion of glucose to 5-HMF is monitored by regular sampling of an aliquot of solution which is immediately cooled to 0° C., redissolved in water and tested by ionic chromatography. The molar yield of 5-HMF after 6 h is 45%. The yield of unwanted humins is 65%.

Example 7: Conversion of Glucose Utilizing a Combination of Aluminium Triflate Al(OTf)$_3$ and Methanesulphonic Acid in DMSO (According to the Invention)

Aluminium triflate Al(OTf)$_3$ (0.26 g, 0.54 mmol) and methanesulphonic acid (0.018 g, 0.19 mmol) are added to a solution of glucose (2.0 g, 11.10 mmol) in DMSO (20 g). The feedstock/Lewis acid catalyst mass ratio is 8. The feedstock/Brønsted acid catalyst mass ratio is 111. The solvent/feedstock mass ratio is 10. The reaction medium is then stirred at 120° C. for 6 h. The conversion of glucose to 5-HMF is monitored by regular sampling of an aliquot of solution which is immediately cooled to 0° C., redissolved in water and tested by ionic chromatography. The molar yield of 5-HMF after 6 h is 90%. The yield of unwanted humins is 10%.

Example 8: Conversion of Glucose Utilizing a Combination of Aluminium Triflate Al(OTf)$_3$ and the Phosphorus-Containing Compound 2 in DMSO (According to the Invention)

Aluminium triflate Al(OTf)$_3$ (0.26 g, 0.54 mmol) and the phosphorus-containing compound 2 (0.072 g, 0.19 mmol) are added to a solution of glucose (2.0 g, 11.10 mmol) in DMSO (20 g). The feedstock/Lewis acid catalyst mass ratio is 8. The feedstock/Brønsted acid catalyst mass ratio is 28. The solvent/feedstock mass ratio is 10. The reaction medium is then stirred at 120° C. for 6 h. The conversion of glucose to 5-HMF is monitored by regular sampling of an aliquot of solution which is immediately cooled to 0° C., redissolved in water and tested by ionic chromatography. The molar yield of 5-HMF after 6 h is 89%. The yield of unwanted humins is 11%.

Example 9: Conversion of Glucose Utilizing a Combination of Aluminium Triflate Al(OTf)$_3$ and the Thiourea Compound 1 in DMSO (According to the Invention)

Aluminium triflate Al(OTf)$_3$ (0.26 g, 0.54 mmol) and the thiourea compound 1 (0.070 g, 0.19 mmol) are added to a solution of glucose (2.0 g, 11.10 mmol) in DMSO (20 g). The feedstock/Lewis acid catalyst mass ratio is 8. The feedstock/Brønsted acid catalyst mass ratio is 29. The solvent/feedstock mass ratio is 10. The reaction medium is then stirred at 120° C. for 6 h. The conversion of glucose to 5-HMF is monitored by regular sampling of an aliquot of solution which is immediately cooled to 0° C., redissolved in water and tested by ionic chromatography. The molar yield of 5-HMF after 6 h is 75%. The yield of unwanted humins is 25%.

The results showing the yield of 5-HMF during sampling carried out after reaction for 6 hours are summarized in Table 1.

TABLE 1

| Example | Feedstock | Catalyst | Solvent | Yield 5-HMF (%) | Yield unwanted products (%) |
|---|---|---|---|---|---|
| 3 Not according to the invention | Glucose | Al(OTf)$_3$ | DMSO | 64 | Humins 36% |
| 4 Not according to the invention | Glucose | MSA | DMSO | 61 | Humins 39% |
| 5 Not according to the invention | Glucose | Phosphorus-containing compound 2 | DMSO | 60 | Humins 40% |
| 6 Not according to the invention | Glucose | Thiourea 1 | DMSO | 45 | Humins 65% |
| 7 according to the invention | Glucose | Al(OTf)$_3$ + MSA | DMSO | 90 | Humins 10% |
| 8 according to the invention | Glucose | Al(OTf)$_3$ + Phosphorus-containing compound 2 | DMSO | 89 | Humins 11% |
| 9 according to the invention | Glucose | Al(OTf)$_3$ + Thiourea 1 | DMSO | 75 | Humins 25% |

The reaction kinetics are quicker and the yield of 5-HMF is greater in the case using a combination of at least one catalyst selected from the homogeneous Lewis acids and at least one homogeneous Brønsted acid catalyst according to the invention in an aprotic polar solvent compared with the homogeneous Lewis acid catalyst alone and the homogeneous Brønsted acid catalyst alone.

The yield of unwanted products is less in the case using a combination of at least one catalyst selected from the homogeneous Lewis acids and at least one homogeneous Brønsted acid catalyst according to the invention in an aprotic polar solvent compared with the catalyst selected from the homogeneous Lewis acids alone and the homogeneous Brønsted acid catalyst alone.

Thus, it unexpectedly appears that it is highly advantageous to use a combination of at least one Lewis acid catalyst and at least one homogeneous Brønsted acid catalyst according to the invention in an aprotic polar solvent compared with the homogeneous Lewis acid catalyst alone and the homogeneous Brønsted acid catalyst alone for the conversion of sugars to 5-HMF.

The invention claimed is:

1. A process for preparing 5-hydroxymethylfurfural from a feedstock comprising at least one sugar, said process comprising reacting the feedstock in the presence of
   at least one homogeneous Lewis acid, which is a compound of formula $M_mX_n$, which is optionally solvated, in which M is an atom of groups 3 to 16 of the periodic table, including lanthanides, m is an integer of 1 to 10, n is an integer of 1 to 10 and X is an anion, which is a hydroxide, halide, nitrate, carboxylate, halocarboxylate, acetylacetonate, alcoholate, phenolate, which is optionally substituted, sulphate, alkylsulphate, phosphate, alkylphosphate, halosulphonate, alkylsulphonate, per-haloalkylsulphonate, bis(per-haloalkylsulphonyl)amide, or arenesulphonate, which is optionally substituted by one or more halogen or haloalkyl groups, and wherein said anions X is identical or different in the case where n is greater than 1,
   and
   at least one homogeneous Brønsted acid catalyst, which is:
   a phosphorus-containing organic compound of the following formula:

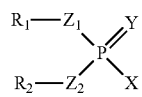

in which
X is OH, SH, SeH or NHR$_3$,
R$_3$ is aryl, aryl sulphonyl or trifluoromethanesulphonyl,
Y is oxygen, sulphur or selenium atom,
Z$_1$ and Z$_2$ are identical or different, and are either an oxygen atom or NR$_4$,
R$_4$ is trifluoromethanesulphonyl, p-toluenesulphonyl or 2-naphthalenesulphonyl,
R$_1$ and R$_2$ are, each independently, alkyl, which is optionally substituted, and is linear, branched or cyclic, or aryl, which is optionally substituted, and is optionally fused;
or
a thiourea of the following formula:

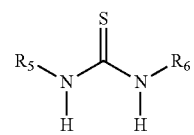

in which
R$_5$ and R$_6$ are, each independently, an aromatic group optionally including one or more heteroatoms, or an alkyl group including at least one heteroatom, and is linear, branched or cyclic, and which R$_5$ and R$_6$ groups are optionally substituted;
or
a sulphonic acid of the following formula:

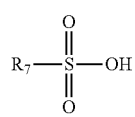

in which R$_7$ is
a halogen,
an alkyl, which is linear, branched or cyclic, and contains 1 to 20 carbon atoms, and is optionally substituted with at least one substituent selected from the group consisting of:
an oxo group,
halogens and,
aryl groups, which are optionally fused, and are optionally substituted with one or more halogen groups and/or one or more linear, branched or cyclic alkyl groups containing 1 to 20 carbon atoms,
an aryl group containing 6 to 14 carbon atoms, which is optionally substituted with at least one substituent selected from the group consisting of:

one or more alkyl groups, which is linear, branched or cyclic, and which contains 1 to 20 carbon atoms, and which is optionally substituted with at least one halogenated group or at least one nitro group,
one or more halogenated groups and
a nitro group;
in the presence of at least one aprotic polar solvent,
at a temperature of 30° C. to 300° C., and at a pressure of 0.1 MPa to 10 MPa.

2. The process according to claim 1, in which said homogeneous Lewis acid of formula $M_mX_n$, is not solvated.

3. The process according to claim 1, in which said sugar is selected from polysaccharides, oligosaccharides and monosaccharides, alone or in a mixture.

4. The process according to claim 3, in which said polysaccharides are selected from starch, inulin, lignocellulosic biomass, cellulose and hemicellulose, alone or in a mixture.

5. The process according to claim 3, in which the monosaccharides are selected from glucose, mannose and fructose, alone or in a mixture.

6. The process according to claim 3, in which the oligosaccharides are selected from saccharose, lactose, maltose, isomaltose, inulobiose, melibiose, gentiobiose, trehalose, cellobiose, cellotriose, cellotetraose and oligosaccharides originating from hydrolysis of polysaccharides originating from the hydrolysis of inulin, cellulose or hemicellulose, alone or in a mixture.

7. The process according to claim 1, in which said homogeneous Brønsted acid catalyst is a phosphorus-containing organic compound of formula:

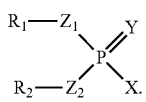

8. The process according to claim 1, in which said homogeneous Brønsted acid catalyst is a thiourea of formula:

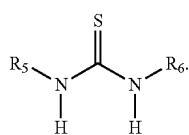

9. The process according to claim 1, in which said homogeneous Brønsted acid catalyst is a sulphonic acid of formula:

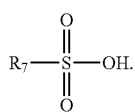

10. The process according to claim 1, which is in the presence of DMSO.

11. The process according to claim 10, in which said homogeneous Lewis acid catalyst is aluminium triflate and said homogeneous Brønsted acid catalyst is selected from methanesulphonic acid, the phosphorus-containing compound 2 of formula:

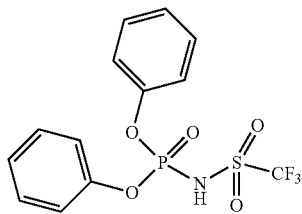 [SMILES: O=P(NS(=O)(=O)C(F)(F)F)(Oc1ccccc1)Oc1ccccc1]

and the thiourea compound 1 of formula:

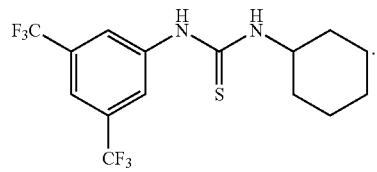 [SMILES: FC(F)(F)c1cc(NC(=S)NC2CCCCC2)cc(C(F)(F)F)c1]

12. The process according to claim 1, in which the aprotic polar solvent has a dipole moment expressed in Debye (D) of greater than 2.00.

13. The process according to claim 1, in which the aprotic polar solvent is selected from pyridine, butan-2-one, acetone, acetic anhydride, N,N,N',N'-tetramethylurea, benzonitrile, acetonitrile, methyl ethyl ketone, propionitrile, hexamethylphosphoramide, nitrobenzene, nitromethane, N,N-dimethylformamide, N,N-dimethylacetamide, sulpholane, N-methylpyrrolidone, dimethylsulphoxide and propylene carbonate alone or in a mixture.

14. The process according to claim 13, in which the aprotic polar solvent is acetone, N,N-dimethylformamide, N,N-dimethylacetamide, sulpholane, N-methylpyrrolidone, dimethylsulphoxide, propylene carbonate or γ-valerolactone, alone or in a mixture.

15. The process according to claim 1, in which the temperature is 50° C. to 200° C., and the pressure is 0.1 MPa to 8 MPa.

16. The process according to claim 1, in which the feedstock is introduced at a solvent/feedstock mass ratio of 0.1 to 200.

17. The process according to claim 1, in which the homogeneous sulphonic acid is introduced at a feedstock/organic catalyst(s) mass ratio of 1 to 1000.

18. The process according to claim 1, wherein the homogeneous Lewis acid is of formula $M_mX_n$, solvated or not, in which M is an atom of groups 6 to 13 of the periodic table, including lanthanides, m is an integer of 1 to 5, n is an integer of 1 to 5 and X is an anion selected from the group consisting of halides, sulphates, alkylsulphonates, and perhaloalkylsulphonates, which is substituted or not by one or more halogen or haloalkyl groups, said anions X being able to be identical or different in the case where n is greater than 1.

19. The process according to claim 1, wherein the homogeneous Lewis acid is $BF_3$, $AlCl_3$, $Al(OTf)_3$, $FeCl_3$, $ZnCl_2$, $SnCl_2$, $CrCl_3$, $CeCl_3$ or $ErCl_3$.

20. The process according to claim 1, for preparing 5-hydroxymethylfurfural from a feedstock comprising at least one sugar, said process comprising reacting the feedstock in the presence of
at least one homogeneous Lewis acid, which is a compound of formula $M_mX_n$, which is optionally solvated, in which M is an atom of groups 3 to 16 of the periodic table, including lanthanides, m is an integer of 1 to 10, n is an integer of 1 to 10 and X is an anion, which is a hydroxide, halide, nitrate, carboxylate, halocarboxylate, acetylacetonate, alcoholate, phenolate, sulphate, alkylsulphate, phosphate, alkylphosphate, halosulphonate, alkylsulphonate, per-haloalkylsulphonate, bis(per-haloalkylsulphonyl)amide, or arenesulphonate, which is optionally substituted by one or more halogen or haloalkyl groups, and wherein said anions X is identical or different in the case where n is greater than 1, and at least one homogeneous Brønsted acid catalyst, which is:

a phosphorus-containing organic compound of the following formula:

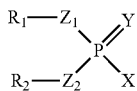

in which

X is OH, SH, SeH or $NHR_3$, $R_3$ is aryl, aryl sulphonyl or trifluoromethanesulphonyl, Y is oxygen, sulphur or selenium atom, $Z_1$ and $Z_2$ are identical or different, and are either an oxygen atom or $NR_4$, $R_4$ is trifluoromethanesulphonyl, p-toluenesulphonyl or 2-naphthalenesulphonyl, $R_1$ and $R_2$ are, each independently, alkyl, which is optionally substituted, and is linear, branched or cyclic, or aryl, which is optionally substituted, and is optionally fused; wherein, when $R_1$ and $R_2$ are substituted, the substituents are one or more groups selected from the group consisting of halogens, —$CX_3$ groups in which X is halogen, nitro group —$NO_2$, —$NHCOCH_3$ group, alkoxy groups, alkyl groups having 1 to 12 carbon atoms, which are linear, branched or cyclic, and aryl groups, or a thiourea of the following formula:

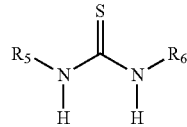

in which $R_5$ and $R_6$ are, each independently, an aromatic group optionally containing one or more heteroatoms, or an alkyl group containing at least one heteroatom, and is linear, branched or cyclic, and which $R_5$ and $R_6$ groups are optionally substituted with one or more groups selected from the group consisting of halogens, —$CX_3$ groups in which X is halogen, nitro group —$NO_2$, —$NHCOCH_3$ group, alkoxy groups, and alkyl groups having 1 to 12 carbon atoms, which are linear or branched;

or a sulphonic acid of the following formula:

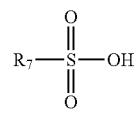

in which $R_7$ is a halogen, an alkyl, which is linear, branched or cyclic, and contains 1 to 20 carbon atoms, and is optionally substituted with at least one substituent selected from the group consisting of:
an oxo group,
halogens and,
aryl groups, which are optionally fused, and are optionally substituted with one or more halogen groups and/or one or more linear, branched or cyclic alkyl groups containing 1 to 20 carbon atoms, an aryl group containing 6 to 14 carbon atoms, which is optionally substituted with at least one substituent selected from the group consisting of:
one or more alkyl groups, which is linear, branched or cyclic, and which contains 1 to 20 carbon atoms, and which is optionally substituted with at least one halogenated group or at least one nitro group,
one or more halogenated groups and
a nitro group;

in the presence of at least one aprotic polar solvent, at a temperature of 30° C. to 300° C., and at a pressure of 0.1 MPa to 10 MPa.

* * * * *